United States Patent [19]

Wei et al.

[11] Patent Number: 4,793,716
[45] Date of Patent: Dec. 27, 1988

[54] THERMAL SHOCK TEST APPARATUS AND THE METHOD OF TESTING

[75] Inventors: George C. Wei, Weston; John Walsh, Milford, both of Mass.

[73] Assignee: GTE Laboratories Incorporated, Waltham, Mass.

[21] Appl. No.: 122,166

[22] Filed: Nov. 18, 1987

[51] Int. Cl.$^4$ .......................... G01N 3/60; G01N 25/72
[52] U.S. Cl. .......................................... 374/45; 374/5; 374/57; 374/138
[58] Field of Search ...................... 374/5, 4, 138, 45, 57

[56] References Cited

U.S. PATENT DOCUMENTS

| 1,327,341 | 1/1920 | MacDonald et al. | 374/5 |
| 2,167,185 | 7/1939 | Preston | 374/5 |
| 3,934,451 | 1/1976 | Bristol et al. | 374/5 |
| 4,314,442 | 2/1982 | Rice | 60/39.05 X |
| 4,519,718 | 5/1985 | Staffin et al. | 374/45 |
| 4,575,257 | 3/1986 | Ogawa et al. | 374/45 |

OTHER PUBLICATIONS

D. P. H. Hasselman, "Unified Theory of Thermal Shock Fracture Initiation and Crack Propagation in Brittle Ceramics", J. Amer. Cer. Soc., 52, 11, 600–604 (Nov. '69).

D. P. H. Hasselman, "Thermal Stress Resistance Parameters for Brittle Refractory Ceramics: A Compendium", Ceramic Bulletin, 49, 12, 1033–1037 (1970).

D. Lewis, III, "Thermal Shock Testing of Optical Ceramics", SPIE, vol. 297, Emerging Optical Materials, 120–124 (1981).

F. A. Strobel, "Thermostructural Evaluation of Spinel Infrared (R) Domes", SPIE, vol. 297, Emerging Optical Materials, 125–136 (1981).

A. F. Emery and A. S. Kobayashi, "Transient Stress Intensity Factors for Edge and Corner Croeles in Quench-Test Specimens", J. Am. Ceram. Soc. 63, 7–8, 410–415 (1980).

Paul F. Becher, David Lewis, III, Kenneth R. Carman, and Armando C. Gonzalez, "Thermal Shock Resistance of Ceramics: Size and Geometry Effects in Quench Tests", Ceramic Bulletin, 59, 5, 542–548 (1980).

Wayne P. Rogers, Ashley F. Emery, Richard C. Bradt, and Albert S. Kobayashi, "Statistical Study of the Thermal Fracture of Ceramic Materials in the Water Quench Test", J. Am. Ceram. Soc., 70 [6] 406–12 (1987).

John R. Brockenbrough, L. Edgar Forsythe, and Richard L. Rolf, "Reliability of Brittle Materials in Thermal Shock", J. Am. Ceram. Soc., 68 [8] 634–37 (1986).

K. T. Faber, M. D. Huang, and A. G. Evans, "Quantitative Studies of Thermal Shock in Ceramics Based on a Novel Test Technique", J. Am. Cer. Soc., 64, 5, 296–301 (1981).

Conduction of Heat in Solids, Second Edition, (1954) by H. S. Carslaw and J. C. Jaeger, Chap. I, "General Theory", 16–25.

Primary Examiner—Daniel M. Yasich
Attorney, Agent, or Firm—Ivan L. Ericson

[57] ABSTRACT

A thermal shock apparatus comprises a hot gas stream impinging means, a hot gas stream impinging control means, a positioning means for the hot gas stream impinging means, and a sample holding means. A sample is subjected to an essentially instantaneous impingement of a hot gas stream upon a predetermined area of the sample when a heat gun is moved past heat deflection foils and positioned above the sample causing a thermal shock within the sample.

7 Claims, 4 Drawing Sheets

THERMAL SHOCK TEST APPARATUS AND THE METHOD OF TESTING

The Government has rights in this invention pursuant to Contract No. N60530-86-C-0022 awarded by the U.S. Navy.

FIELD OF THE INVENTION

This invention relates to an apparatus for applying thermal shock to a sample and a method thereof. More particularly, this invention relates to an apparatus for applying a convective thermal shock to a sample and a method thereof.

BACKGROUND OF THE INVENTION

Many applications of materials such as ceramics, glasses, composites, and polymers involve thermal shock conditions. Stresses may develop in the materials as a result of heating or cooling during applications. If the stresses are sufficiently high and the volume of the material under stresses is sufficiently large, the material will fracture and fail. This is called thermal shock fracture. For example, ceramic materials that are transparent in the infrared range (3-5 micrometer wavelength) are typically used as domes for guidance of missiles. During service, these materials heat up rapidly due to aerodynamic heating, and are subject to thermal shock fracture if the heating rate is too high or the material's resistance to thermal shock is too low. The present invention addresses the need of a simple thermal shock testing method for such infrared dome applications. The results of the invention, the apparatus and method are, however, not limited to the infrared dome application, and may be useful for any thermal shock environments that involve heating in which convective heat transfer is the dominant heat transfer mode.

Hasselman developed a series of equations for calculating thermal shock resistance figures of merit (R parameters) which took into account both mechanical add thermal properties of the materials: D.P.H. Hasselman, "Thermal Stress Resistance Parameters for Brittle Refractory Ceramics, A Compendium," Bulletin of the American Ceramic Society 49, 1033-1037 (1970).

These equation can be applied to a wide variety of thermal shock conditions. These theoretical figures of merit are useful in comparing the theoretical thermal shock behavior of different materials. However, they must be substantiated by the results of thermal shock testing. Therefore, simple thermal shock resistance tests for ranking materials are strongly desirable. This is especially true for the case of infrared transmitting materials for dome applications.

Traditional methods of thermal shock testings include the following: (1) quenching bars into water or oil and determining the strength reduction caused by the quenching (2) laser thermal shock testing involving rapidly heating the central portions of disk samples irradiated with high power laser, (3) wind tunnel testing of actual domes, (4) impinging cold air jet on hot disks, (5) exposing the central portions of disk samples to radiation heat flux from a high-temperature furnace, (6) rapidly heating disk samples in a lamp furnace equipped with focussing mirrors to allow very fast heating, (7) quenching bars into fluidized beds for convective heat transfer, (8) exposing samples to heating in a gas flame of a burner, and (9) fast heating using an array of solar mirrors. These testing methods were discussed in the following references: D. Lewis, "Thermal Shock Testing of Optical Ceramic," SPIE Vol. 297, 120-124 (1981); J. R. Brockenbrough, L. E. Forsythe, and R. L. Rolf, "Reliability of Brittle Materials in Thermal Shock,"

Journal of the American Ceramic Society 69[8]634-637 (1986); K. T. Faber, M. D. Huang, and A. G. Evans, "Quantitative Studies of Thermal Shock in Ceramics Based on a Novel Test Technique," Journal of the American Ceramic Society 64[5]296-301 (1981); and F. A. Strobel "Thermostructural Evaluation of Spinel Infrared Domes", SPIE Vol. 297 pp. 125-136 (1981).

The disadvantages of the above testing methods are:

(1) Quench testing—Results strongly depend on sample size, heat transfer mode complicated by water boiling, heat transfer coefficient is limited if oil is used as the quenching medium, stress corrosion effect unavoidable, and edge or corner effects are undefined.

(2) Laser thermal shock test—Large capital investment for the stable, flat-top type of laser required in the laser thermal shock test. Heat transfer mode involves radiation to the coated layer absorbing the laser radiation and conduction within the sample.

(3) Wind tunnel test—The test involves very sophisticated equipment and instruments, and the calibration and reproducibility of the test conditions are difficult.

(4) Cold-air-jet on hot disk—This test suffers from the fact that thermal conductivity of ceramics typically decreases with increasing temperature. Testing a hot disk does not stimulate the same thermal conditions in a cold disk subjected to aerodynamic heating.

(5) Furnace radiation—Usually insufficient heat flux to initiate thermal shock fracture in ceramics with reasonable strength. The heat transfer mode is primarily radiation.

(6) Lamp furnace heating—This test uses radiation heat transfer.

(7) Quenching in fluidized bed—This test utilizes a low heat transfer coefficient.

(8) Gas burner—The flame temperature is nonuniform; therefore, reproducibility is difficult. (9) Solar mirrors—The test involves very sophisticated equipment and instruments.

SUMMARY OF THE INVENTION

In accordance with one aspect of the present invention, a new and improved thermal shock apparatus comprises a hot gas stream impinging means, a hot gas stream impinging control means, a positioning means, and a sample holding means. The hot gas stream impinging means is adapted to provide impingement of a hot gas stream upon a predetermined impingement area of a sample at a predetermined instant. The hot gas stream impinging control means is adapted to deflect the hot gas stream away from the sample when the hot gas stream impinging control means is positioned between the hot gas stream impinging means and the sample. The hot gas stream impinging control means is adapted to provide an opening for positioning the hot gas stream impinging means close to the ample to provide impingement of the hot gas stream upon the predetermined hot gas stream impingement area of the sample. The positioning means is adapted to position the hot gas stream impinging means, and the sample holding means is adapted to the hot gas stream impinging means and the positioning means to hold the sample in a predetermined position.

In accordance with another aspect of the present invention, a new and improved method for thermal shocking a sample comprises the following steps:

Step 1—A sample is placed in the sample holding means of the thermal shock apparatus of claim 1.

Step 2—The predetermined hot gas stream impingement area of the sample is impinged with the hot gas stream from the hot gas stream impinging means by moving the hot gas stream impinging means past the hot gas stream control means towards the predetermined hot gas stream impingement area of the sample.

Step 3—The impinging hot gas stream is maintained upon the predetermined hot gas stream impingement area of the sample for a predetermined time imparting a thermal shock to the sample.

Figure 1:
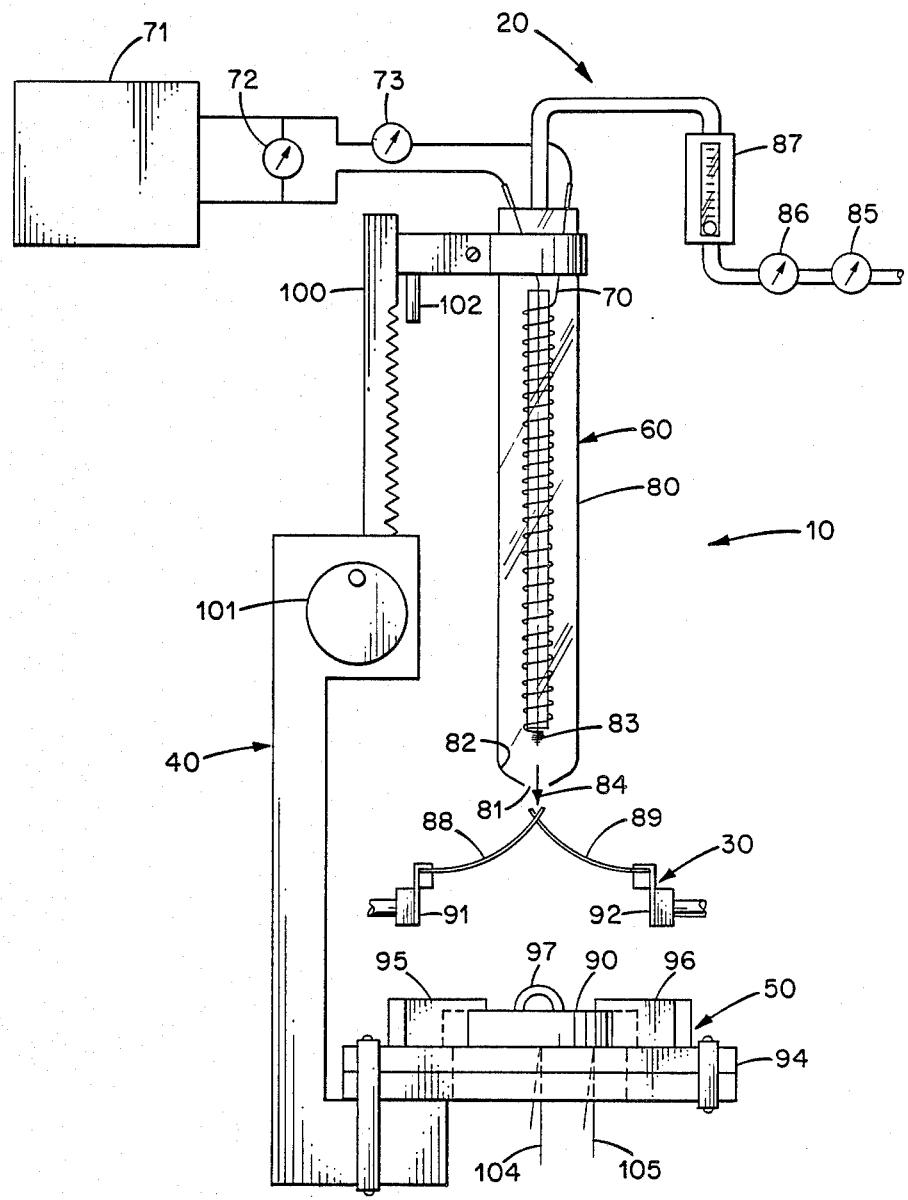
FIG. 1 is a side view of a thermal shock apparatus in accordance with the present invention.

For a better understanding of the present invention, together with other and further objects, advantages and capabilities thereof, reference is made to the following disclosure and appended claims in connection with the above-described drawing.

DETAILED DESCRIPTION OF THE PREFERRED EMBODIMENTS

The method and apparatus of the present invention alleviate the disadvantages associated with the prior-art tests discussed above. The heat transfer mode of the testing method of the present invention is convective. This is particularly important for infrared dome applications in which convection is the dominant mode of heat transfer. The apparatus of the present invention imparts a thermal shock to a given material such as a ceramic, so that the thermal shock can cause mechanical failure of the material by stresses induced by a rapid temperature change experienced by the sample. The thermal stresses developed in the material are controlled by the temperature distribution and thermomechanical properties of the material. The temperature distribution is determined by the initial condition and boundary conditions which, in turn, depend on the dominant heat transfer mode. For radiation heat transfer, the boundary condition is $$\dot{Q} = h(T^4 - T_0^4) \quad (1)$$

where is the flux across the boundary, T the surface temperature, To the temperature of the surrounding medium, h is a constant. For forced convection, which is the case of infrared dome heating during launch of projectile, the boundary condition is $$\dot{Q} = h(T - T_0). \quad (2)$$

In the case of conduction heat transfer, $$k_1/C_{p_1}\rho_1(\partial T/\partial n)_1 = k_2/C_{p_2}(\partial T/\partial n)_2 \quad (3)$$

where k is the thermal conductivity, Cp the heat capacity, $\rho$ the density, $\partial T/\partial n$ the temperature gradient along the normal to the surface of separation, 1 and 2 denote the two media. From Equations (1) to (3), it is obvious that the boundary conditions representing radiation, conduction, and convection types of heat transfer are quite different. Thus, it is essential to devise a test apparatus and procedure that involve a dominant heat transfer mode identical or close to that expected in service.

In addition to the boundary condition, the temperature distributions during transients are affected by the initial condition. It is desirable to have the same initial conditions in the test as in the actual application. For example, infrared domes typically heat up from room temperature during service. Therefore, the simulated test should start with a dome material at room temperature. This is important from thermal property standpoints. Thermal conductivity in ceramics typically decrease with increasing temperature. Thermal conductivity values at high temperatures can be less than ½ or ¼ of those near the ambient temperature. Thus a test involving quenching bars from high temperatures to water bath does not simulate the transient conditions of infrared domes, since the actual application involves heating from room temperature at which the material's thermal conductivity is somewhat higher than the elevated temperatures employed in quench tests.

The apparatus and method of the present invention solved the problems of heat transfer mode, initial conditions, edge or corner effects and stress corrosion effect in the prior-art techniques. It also has a major advantage in terms of simplicity. The apparatus and testing procedure are relatively simple. The geometry of the samples required for the testing of the present invention is relatively simple.

In FIG. 1 is shown a thermal shock apparatus 10 comprising a hot gas stream impinging apparatus 20, the hot gas stream impinging control 30, a positioning mechanism 40, and a sample holder 50. The hot gas stream impinging apparatus 20 comprises a heat gun 60 having a heater coil 70 whose heat output is controlled by power supply 71 with a volt meter 72 and amperage meter 73 to indicate the power being supplied to heater coil 70 and a source of gas controlled by gas regulator 85, pressure gauge 86, and gas flow indicator 87. The quartz envelope 80 has an inside diameter of about .4 inches. The quartz envelope 80 is tapered at one end to reduce the area of the opening to form an orifice 81. The taper has a radius of curvature 82 of approximately 0.16 inch. The heater coil 70 is positioned along the center line of quartz envelope 80 and having its exit end 83 of heater coil 70 positioned approximately 0.5 inches from orifice 81. The temperature and flow rate of hot gas stream 84 is controlled by the gas regulator 85, the pressure gauge 86 and the gas flow indicator 87 in combination with the amount of current applied to heater coil 70. The uniformity of the temperature of the hot gas stream 84 at the orifice 81 region is not only dependent upon the flow rate of the incoming gas in combination with the uniformity of the heat dissipated from the heater coil to the flowing gas along the axis of the coil, it is also dependent upon the geometry of the quartz envelope 80, the position of exit end 83 of heater coil 70, the radius of curvature 82 at the taper of the quartz envelope 80 as well as the diameter of orifice 81.

Figure 3:
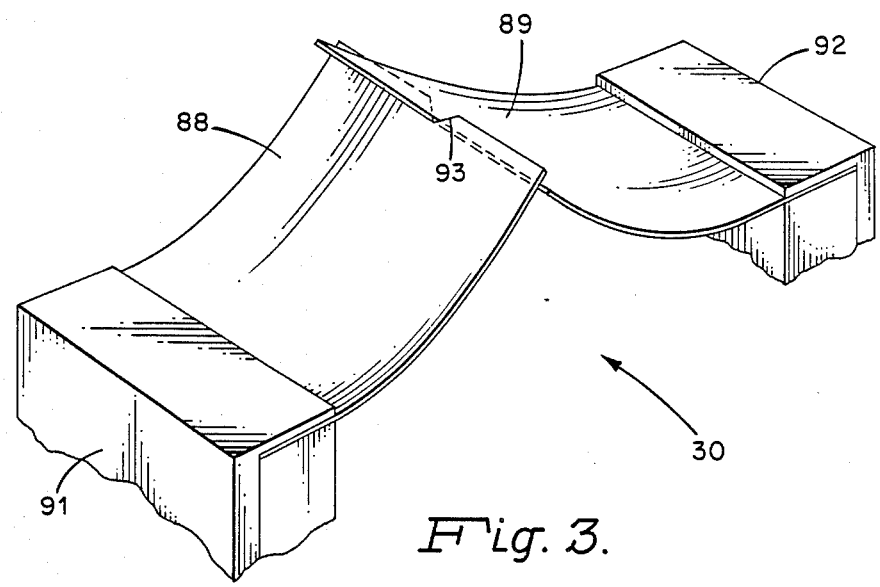
FIG. 3 is a perspective view of the heat deflection means of the thermal shock apparatus of FIG. 1 in accordance with the present invention.

The hot gas stream impinging control 30 comprises two thin foils 88 and 89 which are made from a metal such as stainless steel to act as a hot gas stream deflection shield to prevent the hot gas stream 84 from reaching sample 90 in the position as indicated at FIG. 1. The thin foils 88 and 89 are attached to holders 91 and 92 which are adapted to a fixed position relative to sample holder 50. FIG. 3 shows hot gas stream impinging control 30 in a perspective view of thermal shock apparatus 10 as shown in FIG. 1. As shown in FIG. 3, thin foil 88 has a notch 93 which coacts with thin foil 89 to maintain the position of thin foil 88 and thin foil 89 as shown in FIG. 1 and FIG. 3.

Figure 4:
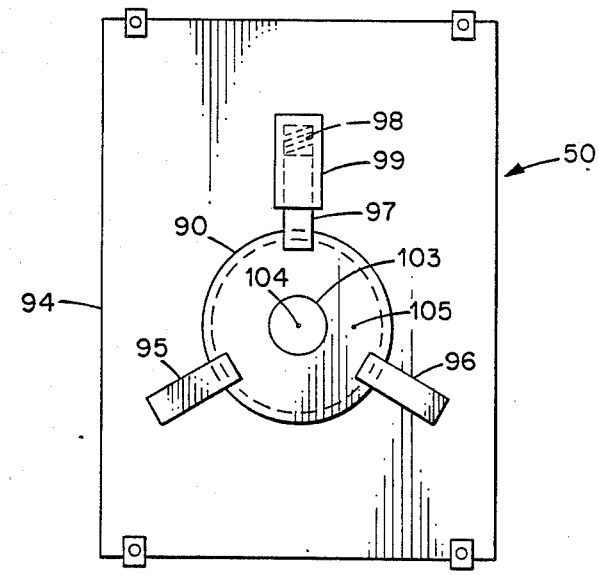
FIG. 4 is a plan view of the sample holder of the thermal shock apparatus of FIG. 1 in accordance with the present invention.

Sample holder 50 as shown in FIG. 1 and FIG. 4 comprises a stage 94 made from a heat resistant material such as quartz and clamps 95, 96 and 97 for holding sample 90 in a predetermined position relative to hot gas stream impinging apparatus 20, hot gas stream impinging control 30 and positioning mechanism 40. Clamp 97 is provided with a spring 98 adapted with a clamp holder 99. The clamps are made from a heat resistant material similar to stage 94 material, and are attached to stage 94.

Figure 2:
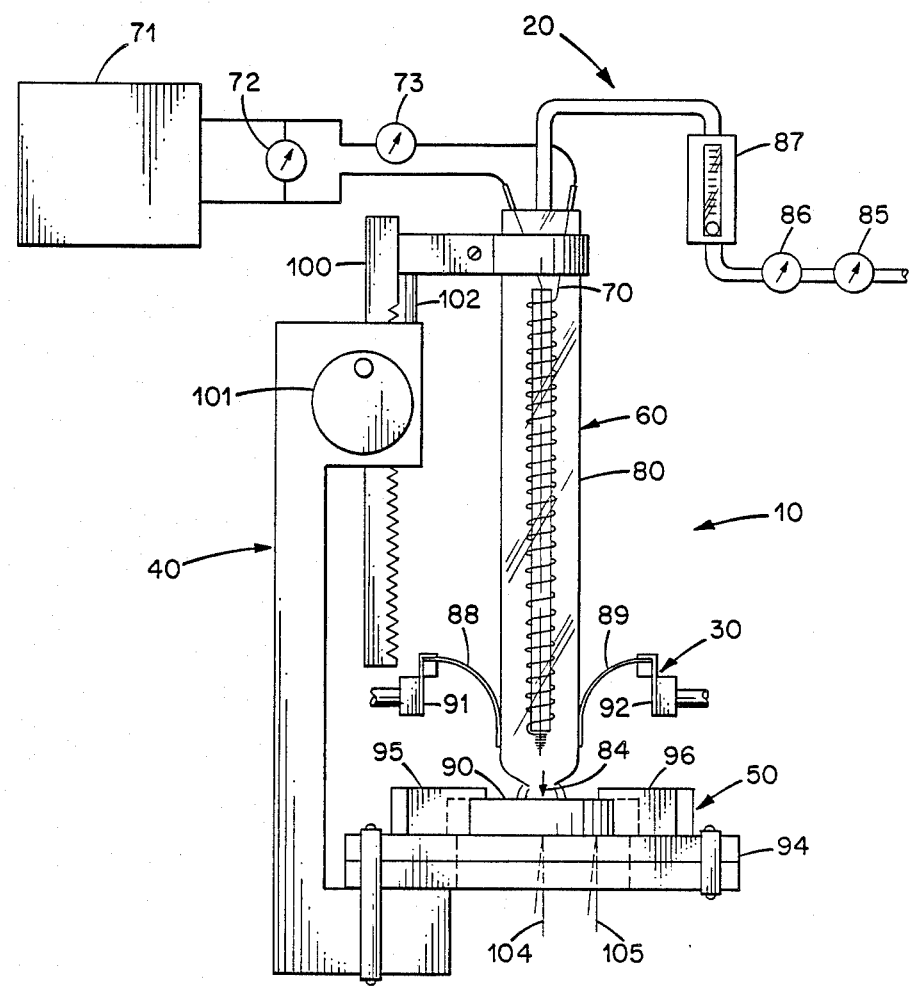
FIG. 2 is a side view of the thermal shock apparatus of FIG. 1 depicting the positioning of the hot gas stream impinging means above the sample in accordance with the present invention.

Positioning mechanism 40, as shown in FIG. 1, has a movable portion 100 adapted to traverse vertically when control wheel 101 is activated. Movable portion 100 is attached to heat gun 60 as depicted in FIG. 1. As shown in FIG. 2, hot gas stream impinging apparatus 20 is relocated directly above sample 90 within less than one second when the movable portion 100 of the positioning mechanism 40 is activated. Stop 102 of movable portion 100 coacts with the stationary portion of the positioning mechanism 40 as depicted in FIG. 2 to locate the orifice 81 of heat gun 60 directly above sample 90 to effect the impingement of hot gas stream 84 upon the predetermined hot gas stream impingement area 103 of sample 90 as shown in FIG. 4. The hot gas stream 84 impinges sample 90 normal to the surface of sample 90 or at another angle of impingement. Thermocouples 104, 105 are located directly under sample 90 as indicated in FIG. 1 and FIG. 4 to facilitate temperature measurement of sample 90 before and during the hot gas stream impingement upon the predetermined hot gas stream impingement area 103 of sample 90.

As shown in FIG. 2, the exit end of quartz envelope 80 containing orifice 81 is rapidly moved from its position as shown in FIG. 1 to a position directly above sample 90 as depicted in FIG. 2 by the operation of control wheel 101 of positioning mechanism 40. The exit end of heat gun 6 is moved vertically past foil 88 and 89 which move from their position as depicted in FIG. 1 to the new position as depicted in FIG. 2 exposing the predetermined hot gas stream impingement area 103 of sample 00 to the hot gas stream 84 of heat gun 60 thereby imparting a thermal shock to sample 90.

The heat source is capable of heating the upper surface of sample 90 to $\simeq 750°$ C. when the orifice 81 of the heat gun 60 is located 5/32" directly above the area 10 of the top surface of the sample 90. Other types of hot gas heaters employing a coil heater, a quartz envelope, and argon gas can produce a hot gas stream of argon at temperatures up to 1000° C. If a ceramic, such as alumina, zirconia, or yttria, is used as an envelope, and a gas, such as argon helium, hydrogen, or nitrogen hydrogen mixture, is used as the hot gas, temperatures of the hot gas stream up to 1900-2000° C. are expected. The heat gun 60 is raised and lowered by the upward and downward motion of positioning mechanism 40 such as a press which has been fitted with a control wheel 101 as opposed to a lever. A stop 102 on the movable portion 100 ensures a constant distance between the orifice 81 of the heat gun 60 and the upper surface of the sample 90 for each test. The orifice 81 of the heat gun 60 is about 0.146 inches in diameter and the orifice end of the hot air gun 60 is rounded to provide a more uniform distribution of the hot gas stream from the orifice.

The thin foils 88 and 89 acting as heat deflection shutters assist in cooling the sample 90 to room temperature after each test. These are purposely made very flexible so that the heat gun 60 can move up and down without encountering undue obstruction.

Two thermocouples 104, 105 are in contact with the lower surface of the sample 90 during the test to record temperatures at the center and at an area adjacent to the periphery of sample 90. A chart recorder is used for recording these temperatures. A chart of the hot gas stream 84 temperature vs applied voltage for the heat gun 60 was made prior to the use of thermal shock apparatus 10 for the thermal shock tests. This calibration was checked periodically during sample testing.

The test sample was positioned in a sample holder 50, which consists of a three-point, lightly spring-loaded clamping fixture made of quartz. This holder is located below and directly in line with the heat gun 60, and when the heat gun 60 is in the raised position, the thin foils 88, 89 isolate the sample from the hot gas stream 84 of the raised heat gun 60. This is necessary since the hot gas stream 84 temperature must be maintained between tests in order for temperature stabilization to take place before the succeeding step in the test can be carried out.

Figure 5:
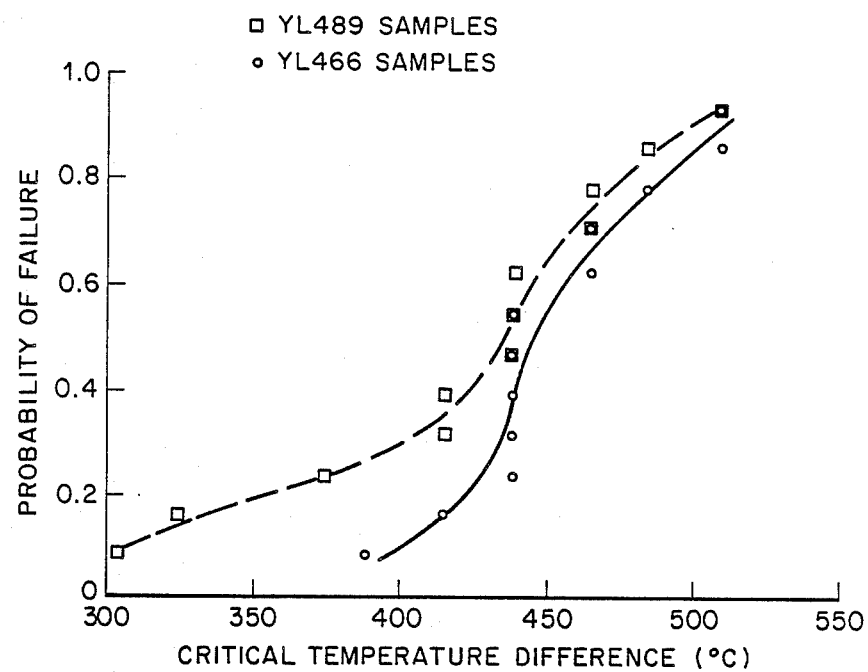
FIG. 5 is a curve of the probability of failure of samples as a function of the critical temperature difference in accordance with the present invention.

This thermal shock test apparatus 10 utilizing a heat gun 60 such as a serpentine heater Sylvania No. 010226 is capable of thermal shocking ceramic samples such as lanthana-doped yttria to the point of fracture. One example is described below. Standard $La_2O_3$-doped $Y_2O_3$ (containing 9 mole percent $La_2O_3$) sample disks (¾ inch diameter by 2 mm thick) typically fractured during the test when the hot gas stream temperature was 350-530° C. Fracture initiated from the central portion of the sample, eliminating edge or corner effects encountered in other tests such as quenching tests. The time to fracture ranged from about 10 sec to about 90 sec, depending on the test sample. The sample holder 50 was stationary and the heat gun 60 was mounted on movable portion 100 which was injected toward the sample 90. This configuration produced a good repeatability of the test conditions. The test method consisted of (1) injecting the hot gas gun 60 toward the sample 90 (2) maintaining the hot gas gun 60 at a position ($\sim 5/32"$) above the sample 90 for 2 min, (3) if the sample 90 did not fracture in the 2 min exposure period, raising the hot gas gun 60 to let the sample cool to ambient, and then restarting steps (1) to (2) again at hot gas temperatures incrementally higher until the sample 90 fractured, and (4) if the sample 90 fractured (this was typically observed by visual examination, or the acoustic emission of fracture typically produced a sound that was audible to the observer), raising the hot gas gun 60 and removing the sample 90 when it cooled to ambient. The test results are expressed in terms of critical temperature difference ($\Delta Tc$) which is defined as the critical hot gas temperature (the hot gas stream temperature at which the sample fractures) minus the initial temperature (room temperature). The results of thermal shock testing on two types of La$_2$O$_3$-doped Y$_2$O$_3$, YL466 and YL489, are listed in Table 1. The probability of thermal shock fracture (probability of failure) can be calculated by the standard procedure of (1) ranking the ΔTc, and (2) calculating the failure probability by R/(1+N) where R is the order in the ranking, and N the total number of test samples. One example of the probability of failure vs critical temperature difference (ΔTc) is shown in FIG. 5.

TABLE 1

RESULTS OF HOT-GAS JET THERMAL SHOCK TESTING
Critical Temperature Difference (°C.)
ΔTc, (critical hot gas stream temperature - room temperature)

| Sample Type YL489 ΔTc | Sample Type YL466 ΔTc |
|---|---|
| 508 | 508 |
| 483 | 508 |
| 464 | 483 |
| 464 | 464 |
| 438 | 464 |
| 438 | 438 |
| 438 | 438 |
| 415 | 438 |
| 415 | 438 |
| 374 | 438 |
| 324 | 415 |
| 303 | 389 |

An alternative procedure consists of testing with a high ΔTc. For example, ΔTc=508° (hot gas stream temperature =530° C.) is used for all samples, and the time to fracture is measured. The absolute value of an average time of fracture provides a measure of the resistance to fracture.

The structure of the apparatus can be easily be modified for automation. For example, the press can be replaced with a solenoid device that injects the heat gun upon activating the solenoid. The hot gas stream impinging control 30 can be replaced with a diaphragm that opens up automatically when the heat gun 60 is injected toward sample 90. Heaters of higher temperature capabilities such as tungsten-wire heater or platinum-wire heater with quartz, alumina, zirconia, or yttria envelopes can be used for producing hot air (platinum-wire heater) or hot gas (e.g. Ar, He, or N$_2$ with tungsten heater) at high temperatures (>1000° C.) required in thermal shock testings of materials such as SiC or Si$_3$N$_4$ that are more resistant to thermal shock than yttria. The thermal shock apparatus 10 and the methods described are not limited to ceramics, other materials such as glass, composites, and polymers can also be tested.

While there has been shown and described what is at present considered the referred embodiment of the invention, it will be obvious to those skilled in the art that various changes and modifications may be made therein without departing from the scope of the invention as defined by the appended claims.

What is claimed is:

1. A thermal shock apparatus comprising
a hot gas stream impinging means for providing an impingement of a hot gas stream upon a predetermined hot gas stream impingement area of a sample, said sample having an upper surface containing a center portion, said predetermined hot gas stream impingement area being located on said center portion of said upper surface of said sample;
a hot gas stream impinging control means being adapted to deflect said hot gas stream away from said sample when said hot gas stream impinging control means is positioned between said hot gas stream impinging means and said sample, and being adapted to provide an opening from positioning said hot gas stream impinging means close to said sample to provide impingement of said hot gas stream upon said predetermined hot gas stream impingement area of said sample;
a positioning means being connected to said hot gas stream impinging means and being adapted to position said hot gas stream impinging means; and
a sample holding means being connected to said positioning means to hold said sample in a predetermined position.

2. A thermal shock apparatus in accordance with claim 1 wherein said hot gas impinging means comprises a heat gun and a controlled source of gas.

3. A thermal shock apparatus in accordance with claim 1 wherein said sample holding means has a positioning means for positioning said sample to maintain a planar position of said sample which is normal to said hot gas stream.

4. A thermal shock apparatus comprising
a hot gas stream impinging means for providing an impingement of a hot gas stream upon a predetermined hot gas stream impingement area of a sample;
a hot gas stream impinging control means being adapted to deflect said hot gas stream away from said sample when said hot gas stream impinging control means is positioned between said hot gas stream impinging means and said sample, and being adapted to provide an opening for positioning said hot gas stream impinging means close to said sample to provide impingement of said hot gas stream upon said predetermined hot gas stream impingement area of said sample;
a positioning means being connected to said hot gas stream impinging means and being adapted to position said hot gas stream impinging means; and
a sample holding means being connected to said positioning means to hold said sample in a predetermined position; said hot gas impinging control means comprising two thin foils adapted to deflect said hot gas stream away from said sample in one position and adapted to provide an opening for positioning said gas impinging means close to said predetermined hot gas impingement area of said sample.

5. A thermal shock apparatus in accordance with claim 4 wherein said sample holding means has a positioning means for positioning said sample to maintain a planar position of said sample which is normal to said hot gas stream.

6. A method for thermal shocking a sample comprises the following steps:
Step 1—placing a sample in said sample holder of said thermal shock apparatus of claim 1;
Step 2—moving said hot gas stream impinging means past said hot gas stream impinging control means towards said predetermined hot gas stream impingement area of said sample;
Step 3—impinging said predetermined hot gas stream impingement area of said sample with said hot gas stream from said hot gas stream impinging means; and Step 4—maintaining said hot gas stream upon said predetermined hot gas stream impingement area of said sample for a predetermined time imparting a thermal shock within said sample.

7. A method in accordance with claim 6 wherein said hot gas stream impinging means moves past said hot gas stream impinging control means towards said predetermined hot gas stream impingement area of said sample within less than one second.

* * * * *